United States Patent
Auclair et al.

(10) Patent No.: US 8,227,433 B2
(45) Date of Patent: Jul. 24, 2012

(54) USE OF INHIBITORS AND ANTISENSE OLIGONUCLEOTIDES OF BTK FOR TREATING PROLIFERATIVE MASTOCYTOSIS

(75) Inventors: Christian Auclair, Paris (FR); Frédéric Subra, Paris (FR)

(73) Assignees: Centre National de la Recherche Scientifique (CNRS), Paris (FR); Paris-Sud, Universite, Orsay (FR); Ecole Normale Superieure de Cachan, Cachan (FR)

( * ) Notice: Subject to any disclaimer, the term of this patent is extended or adjusted under 35 U.S.C. 154(b) by 1213 days.

(21) Appl. No.: 10/555,205

(22) PCT Filed: May 3, 2004

(86) PCT No.: PCT/IB2004/001782
§ 371 (c)(1),
(2), (4) Date: Jul. 13, 2006

(87) PCT Pub. No.: WO2004/096253
PCT Pub. Date: Nov. 11, 2004

(65) Prior Publication Data
US 2010/0216733 A1    Aug. 26, 2010

(30) Foreign Application Priority Data
May 2, 2003   (EP) .................................. 03291066

(51) Int. Cl.
*C12N 15/11* (2006.01)
*C07H 21/02* (2006.01)
*C07H 21/04* (2006.01)

(52) U.S. Cl. ..................... 514/44; 536/24.1; 536/24.5

(58) Field of Classification Search ............... 514/44
See application file for complete search history.

(56) References Cited

U.S. PATENT DOCUMENTS 6,303,652 B1   10/2001   Uckun et al.
6,828,151 B2 *   12/2004   Borchers et al. ............... 435/458

FOREIGN PATENT DOCUMENTS
WO        WO 01/66107        *    9/2001

OTHER PUBLICATIONS

Heinonen, J.E. et al., FEBS Letters, Elsevier Science Publishers, Amsterdam, NL, vol. 527, No. 1-3, Sep. 11, 2002, pp. 274-278.
Ghosh, S. et al., ACTA Crystalographica Section C. Crystal Structure Communications, Munksgaard, Copenhagen, DK, vol. C55, No. Part 8, Aug. 15, 1999, pp. 1364-1365.
Ghosh, S. et al., ACTA Crystalographica Section C. Crystal Structure Communications, Munksgaard, Copenhagen, DK, vol. C56, No. Part 10, 2000, pp. 1254-1257.

* cited by examiner

*Primary Examiner* — Terra Cotta Gibbs
(74) *Attorney, Agent, or Firm* — Birch, Stewart, Kolasch & Birch, LLP

(57) ABSTRACT

The present invention relates to a method for treating proliferative mastocytosis comprising administering a Bruton tyrosine kinase (BTK) inhibitor, a BTK antisense to a mammal in need of such treatment. The invention is more particularly suited for treating category II, III and IV mastocytosis.

17 Claims, 3 Drawing Sheets

Bruton's tyrosine kinase

Figure 1:
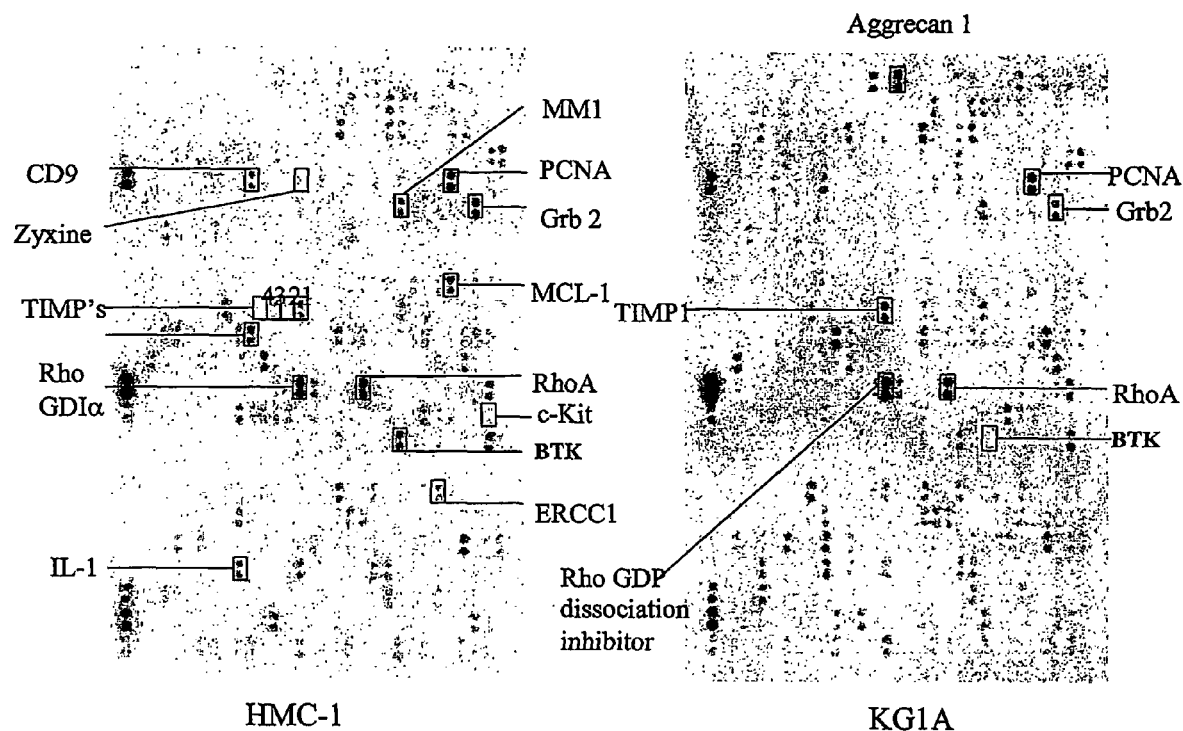

SEQUENCE LISTING

```
<160> NUMBER OF SEQ ID NOS: 2

<210> SEQ ID NO 1
<211> LENGTH: 32
<212> TYPE: DNA
<213> ORGANISM: Artificial Sequence
<220> FEATURE:
<223> OTHER INFORMATION: Antisense primer

<400> SEQUENCE: 1
agaatcactg cggccatagc ttcttctttc tg                                   32
```

<210> SEQ ID NO 2
<211> LENGTH: 2591
<212> TYPE: DNA
<213> ORGANISM: homo sapiens

<400> SEQUENCE: 2

| | | | | | |
|---|---|---|---|---|---|
| ctcagactgt | ccttcctctc | tggactgtaa | gaatatgtct | ccagggccag | tgtctgctgc | 60 |
| gatcgagtcc | caccttccaa | gtcctggcat | ctcaatgcat | ctgggaagct | acctgcatta | 120 |
| agtcaggact | gagcacacag | gtgaactcca | gaaagaagaa | gctatggccg | cagtgattct | 180 |
| ggagagcatc | tttctgaagc | gatcccaaca | gaaaaagaaa | acatcacctc | taaacttcaa | 240 |
| gaagcgcctg | tttctcttga | ccgtgcacaa | actctcctac | tatgagtatg | actttgaacg | 300 |
| tgggagaaga | ggcagtaaga | agggttcaat | agatgttgag | aagatcactt | gtgttgaaac | 360 |
| agtggttcct | gaaaaaaatc | ctcctccaga | aagacagatt | ccgagaagag | gtgaagagtc | 420 |
| cagtgaaatg | gagcaaattt | caatcattga | aggttccct | tatcccttcc | aggttgtata | 480 |
| tgatgaaggg | cctctctacg | tcttctcccc | aactgaagaa | ctaaggaagc | ggtggattca | 540 |
| ccagctcaaa | aacgtaatcc | ggtacaacag | tgatctggtt | cagaaatatc | acccttgctt | 600 |
| ctggatcgat | gggcagtatc | tctgctgctc | tcagacagcc | aaaaatgcta | tgggctgcca | 660 |
| aatttttggag | aacaggaatg | gaagcttaaa | acctgggagt | tctcaccgga | agacaaaaaa | 720 |
| gcctcttccc | ccaacgcctg | aggaggacca | gatcttgaaa | aagccactac | cgcctgagcc | 780 |
| agcagcagca | ccagtctcca | caagtgagct | gaaaaaggtt | gtggccctttt | atgattacat | 840 |
| gccaatgaat | gcaaatgatc | tacagctgcg | aagggtgat | gaatatttta | tcttggagga | 900 |
| aagcaactta | ccatggtgga | gagcacgaga | taaaaatggg | caggaaggct | acattcctag | 960 |
| taactatgtc | actgaagcag | aagactccat | agaaatgtat | gagtggtatt | ccaaacacat | 1020 |
| gactcggagt | caggctgagc | aactgctaaa | gcaagagggg | aaagaaggag | gtttcattgt | 1080 |
| cagagactcc | agcaaagctg | gcaaatatac | agtgtctgtg | tttgctaaat | ccacagggga | 1140 |
| ccctcaaggg | gtgatacgtc | attatgttgt | gtgttccaca | cctcagagcc | agtattacct | 1200 |
| ggctgagaag | cacctttttca | gcaccatccc | tgagctcatt | aactaccatc | agcacaactc | 1260 |
| tgcaggactc | atatccaggc | tcaaatatcc | agtgtctcaa | caaaacaaga | atgcaccttc | 1320 |
| cactgcaggc | ctgggatacg | gatcatggga | aattgatcca | aaggacctga | ccttcttgaa | 1380 |
| ggagctgggg | actggacaat | tggggtagt | gaagtatggg | aaatgagag | gccagtacga | 1440 |
| cgtggccatc | aagatgatca | agaaggctc | catgtctgaa | gatgaattca | ttgaagaagc | 1500 |
| caaagtcatg | atgaatcttt | cccatgagaa | gctggtgcag | ttgtatggcg | tctgcaccaa | 1560 |
| gcagcgcccc | atcttcatca | tcactgagta | catggccaat | ggctgcctcc | tgaactacct | 1620 |
| gagggagatg | cgccaccgct | tccagactca | gcagctgcta | gagatgtgca | aggatgtctg | 1680 |
| tgaagccatg | gaatacctgg | agtcaaagca | gttccttcac | cgagacctgg | cagctcgaaa | 1740 |
| ctgtttggta | aacgatcaag | gagttgttaa | agtatctgat | ttcggcctgt | ccaggtatgt | 1800 |
| cctggatgat | gaatacacaa | gctcagtagg | ctccaaattt | ccagtccggt | ggtccccacc | 1860 |
| ggaagtcctg | atgtatagca | agttcagcag | caaatctgac | atttgggctt | ttggggtttt | 1920 |
| gatgtgggaa | atttactccc | tggggaagat | gccatatgaa | gatttacta | acagtgagac | 1980 |
| tgctgaacac | attgcccaag | gcctacgtct | ctacaggcct | catctggctt | cagagaaggt | 2040 |
| atataccatc | atgtacagtt | gttggcatga | gaaagcagat | gagcgtccca | cttttcaaat | 2100 |
| tcttctgagc | aatattctag | atgtcatgga | tgaagaatcc | tgagctcgcc | aataagcttc | 2160 |

```
ttggttctac ttctcttctc cacaagcccc aatttcactt tctcagagga aatcccaagc    2220
ttaggagccc tggagccttt gtgctcccac tcaatacaaa aaggcccctc tctacatctg    2280
gggatgcacc tcttctttga ttccctggga tagtggcttc tgagcaaagg ccaaaaaatt    2340
attgtgcctg aaatttcccg agagaattaa gacagactga atttgcgatg aaaatatttt    2400
ttaggaggga ggatgtaaat agccgcacaa aggggtccaa cagctctttg agtaggcatt    2460
tggtagagct tgggggtgtg tgtgtggggg tggaccgaat ttggcaagaa tgaaatggtg    2520
tcataaagat gggaggggag ggtgttttga taaaataaat tctagaaagc ttaaaaaaaa    2580
aaaaaaaaaa a                                                         2591
```

USE OF INHIBITORS AND ANTISENSE OLIGONUCLEOTIDES OF BTK FOR TREATING PROLIFERATIVE MASTOCYTOSIS

The present invention relates to a method for treating proliferative mastocytosis comprising administering a Bruton tyrosine kinase (BTK) inhibitor, a BTK antisense oligonucleotide or a vector expressing said antisense to a mammal in need of such treatment. The invention is more particularly suited for treating category II, III and IV mastocytosis.

Mastocytosis are a very heterogeneous group of disorders characterized by an abnormal accumulation of mast cells in different tissues, mainly in the skin and the bone marrow, but also in spleen, liver, lymph nodes, and the gastrointestinal tract, depending on the nature of the disease. They can affect humans of either sex at any age. Neoplasms of mast cells (MC) can be acute or chronic. Acute mast cell neoplasms are designated as MC leukemia. Chronic mast cell neoplasms may be localized or generalized. Cutaneous mastocytosis is the commonest localized neoplasm and is often found in children in which it often remits and never relapses. Mastocytosis are usually acquired diseases, but some rare familial cases have been described.

With regard to the extreme heterogeneity of mast cell neoplasms, it is important to classify these diseases. One of the most used classification is the one by Metcalfe (Metcalfe, J Invest Dermatol. 96: 2S-4S, 1991) that distinguishes four categories of mastocytosis :

The category I is composed by two sub-categories (IA and IB). Category IA is made by diseases in which mast cell infiltration is strictly localized to the skin. This category represents the most frequent form of the disease and includes: i) urticaria pigmentosa, the most common form of cutaneous mastocytosis, particularly encountered in children, ii) diffuse cutaneous mastocytosis, iii) solitary mastocytoma and iv) some rare subtypes like bullous, erythrodermic and teleangiectatic mastocytosis. These forms are characterized by their excellent prognosis with spontaneous remissions in children and a very indolent course in adults. Long term survival of this form of disease is generally comparable to that of the normal population and the translation into another form of mastocytosis is rare. Category IB is represented by indolent systemic disease (SM) with or without cutaneous involvement. These forms are much more usual in adults than in children. The course of the disease is often indolent, but sometimes signs of aggressive or malignant mastocytosis can occur, leading to progressive impaired organ function.

The category II includes. Mastocytosis with an associated hematological disorder, such as a myeloproliferative or myelodysplastic syndrome, or acute leukemia. These malignant mastocytosis does not usually involve the skin. The progression of the disease depends generally on the type of associated hematological disorder that conditiones the prognosis.

The category III is represented by aggressive systemic mastocytosis in which massive infiltration of multiple organs by abnormal mast cells is common. In patients who pursue this kind of aggressive clinical course, peripheral blood features suggestive of a myeloproliferative disorder are more prominent. The progression of the disease can be very rapid, similar to acute leukemia, or some patients can show a longer survival time.

Finally, the category IV of mastocytosis includes the mast cell leukemia, characterized by the presence of circulating mast cells and mast cell progenitors representing more than 10% of the white blood cells. This entity represents probably the rarest type of leukemia in humans, and has a very poor prognosis, similar to the rapidly progressing variant of malignant mastocytosis. Mast cell leukemia can occur either de novo or as the terminal phase of urticaria pigmentosa or systemic mastocytosis.

Since categories II and III do not differ prognostically, the classification of Metcalfe can be further simplified as shown in Table I, according to the recommendations of Horny et al (Horny et al, Am J Surg Pathol. 22: 1132-40, 1998).

TABLE I

| Localized (category I) | Generalized (categories II, III, IV) |
| --- | --- |
| Cutaneous mastocytosis<br>Solitary mastocytoma<br>Urticaria pigmentosa | Systemic mastocytosis (with or without cutaneous involvement)<br>Indolent<br>Aggressive<br>Mast cell leukemia |

Mast cells (MC) are tissue elements derived from a particular subset of hematopoietic stem cells that express CD34, c-kit and CD13 antigens (Kirshenbaum et al, Blood. 94: 2333-2342, 1999 and Ishizaka et al, Curr Opin Immunol. 5: 937-43, 1993). Immature MC progenitors circulate in the bloodstream and differentiate in tissues. These differentiation and proliferation processes are under the influence of cytokines, one of utmost importance being Stem Cell Factor (SCF), also termed Kit ligand (KL), Steel factor (SL) or Mast Cell Growth Factor (MCGF). SCF receptor is encoded by the protooncogene c-kit, that belongs to type III receptor tyrosine kinase subfamily (Boissan and Arock, J Leukoc Biol. 67: 135-48, 2000). This receptor is also expressed on others hematopoietic or non hematopoietic cells. Ligation of c-kit receptor by SCF induces its dimerization followed by its transphosphorylation, leading to the recruitement and activation of various intracytoplasmic substrates. These activated substrates induce multiple intracellular signaling pathways responsible for cell proliferation and activation (Boissan and Arock, 2000). Mast cells are characterized by their heterogeneity, not only regarding tissue location and structure but also at the functional and histochemical levels (Aldenborg and Enerback., Histochem. J. 26: 587-96, 1994 ; Bradding et al. J Immunol. 155: 297-307, 1995 ; Irani et al, J Immunol. 147: 247-53, 1991 ; Miller et al, Curr Opin Immunol. 1: 637-42, 1989 and Welle et al, J Leukoc Biol. 61: 233-45, 1997).Differentiation, survival and proliferation of MC depend greatly on SCF (Torrey et al, 1990). The receptor for SCF is c-kit, encoded by the protooncogene c-kit; it belongs to type III receptor tyrosine kinase subfamily (Baghestanian et al, 1996). Numerous studies have been performed regarding the neoplastic mechanism of mastocytosis, searching for genetic abnormalities of c-kit (mutation, deletion). The existence of such abnormalities was suggested because they were previously found in rodent or human leukemic MC lines. In human mastocytosis, mutations of c-kit have been described in vivo in various forms of mastocytosis (cutaneous mastocytosis, systemic indolent or systemic aggressive mastocytosis). Among the mutations found, the most common is the activating mutation Asp to Val at codon 816. In addition, one report has described a mutation in the juxtamembrane domain of c-kit (Val to Gly at codon 560) in human mastocytosis (Valent et al, 1994). Furthermore, Longley et al (Pauls et al, 1999) have showed that the point mutations in position 816.

While research is now mainly focusing on the c-kit receptor, the role of BTK in proliferative mast cells has been overlooked. Indeed, BTK is mainly known because it is implicated in B cell development, for a review see Maas A et al, Dev Immunol 2001; 8(3.-4): 171-81. BTK is also considered to be involved in the degranulation of mast cells. For example, Hata D et al, J Exp Med 1998 Apr. 20;187(8):1235-47 have shown the involvement of BTK in FcsRI-dependent mast cell degranulation and cytokine production. Consequently, inhibitors of BTK are proposed in the art for the treatment of allergic disorders. Among such inhibitors, we can cite compound D-58 (2,4,6-trihydroxy-alpha-p-methoxyphenylacetophenone), Malaviya R. et al, Am J Ther 2001 November-December; 8(6): 417-24. In addition, Silva Junior H T et al, Am J Med Sci 1997 May; 313(5): 289-301 and Bertolini G. et al, J Med Chem 1997 Jun 20; 40(13): 2011-6 have also shown that the immunomodulatory activity of leflunomide is attributed to its primary metabolite A77 1726, which is a malononitrilamide. Other leflunomide metabolite analogs have been found to inhibit BTK (Ghosh S. et al, Acta Crystallogr C 2000 October; 56 (Pt 10): 1254-7), namely 1-cyano-2-hydroxy-N-[4-(methylsulfonyl) phenyl]but-2-enamide, 1-cyano-2-hydroxy-N-[3-(methylsulfonyl)phenyl]but-2-enamide, and N-[3-bromo-4-(trifluoromethoxy)phenyl]-1-cyano-2-hydroxybut-2-enamide.

Here, the invention provides a new therapeutic application for BTK inhibitors for the treatment of proliferative mast cells disorders.

This discovery is based on the unexpectedly finding that BTK is strongly over-expressed in proliferative mast cells lines compared to normal mature mast cell lines.

Furthermore, using antisens oligonucleotide directed against BTK, we were able to significantly decrease the size of tumors. Therefore, the invention provides a new route for the treatment of proliferative mastocytosis and more particularly mast cell leukemia.

Description

The present invention relates to a method for treating proliferative mastocytosis comprising administering a BTK inhibitor, a BTK antisense oligonucleotide or a vector expressing said antisense to a mammalian in need of such treatment.

In a first embodiment, the invention contemplates the above method using BTK inhibitors which can be selected for example from malononitrilamides and more particularly from leflunomide analogs such as:
1-cyano-2-hydroxy-N-[4-(methylsulfonyl)phenyl]but-2-enamide,
1-cyano-2-hydroxy-N-[3-(methylsulfonyl)phenyl]but-2-enamide, and
N-[3-bromo-4-(trifluoromethoxy)phenyl]-1-cyano-2-hydroxybut-2-enamide.

It can also be selected from phenylacetophenone derivatives.

In a further embodiment, the invention contemplates a method for treating mastocytosis comprising administering to a mammalian in need of such treatment a compound that is a selective, potent and non toxic inhibitor of BTK obtainable by a screening method which comprises:
a) bringing into contact (i) BTK and (ii) at least one compound to be tested; under conditions allowing the components (i) and (ii) to form a complex, and
b) selecting compounds that inhibit BTK at a concentration below 10 µM or 5 µM, preferably at concentrations below 1 µM.

This screening method can be practiced in vitro using standard biochemical techniques such as immunoprecipitation and western blot. Preferably, the amount of BTK phosphorylation is measured.

Alternatively, the invention contemplates a method for treating proliferative mastocytosis as depicted above wherein the screening is accomplished in vivo. The screening comprises performing a proliferation assay with cells expressing a mutant c-kit (for example in the transphosphorylase domain), which mutant is a permanent activated c-kit, with a plurality of test compounds to identify a subset of candidate compounds targeting BTK, each having an IC50<10 µM, preferably an IC50<1 µM, by measuring the extent of cell death:

Cells that can be used in this regards can be selected from:
HMC-1, a factor-independent cell line derived from a patient with mast cell leukemia, expresses a juxtamembrane mutant c-kit polypeptide that has constitutive kinase activity (Furitsu T et al, J Clin Invest. 1993; 92: 1736-1744 ; Butterfield et al, Establishment of an immature mast cell line from a patient with mast cell leukemia. Leuk Res. 1988; 12: 345-355 and Nagata et al, Proc Natl Acad Sci U S A. 1995; 92: 10560-10564).

P815 cell line (mastocytoma naturally expressing c-kit mutation at the 814 position) has been described in Tsujimura et al, (1994), Blood 83, 2619-2626.

and cells lines derived thereof.

Here, the extent of cell death can be measured by 3H thymidine incorporation, the trypan blue exclusion method or flow cytometry with propidium iodide. These are common techniques routinely practiced in the art.

In addition, it is also possible to perform a proliferation assay with mature mast cells or CD4+cells with the compounds identified above, and to select a subset of compounds that do not affect significantly the viability of these cells. Tests with normal mast cells or CD4+ cells can routinely be used as control for toxicity.

In a second embodiment, the method of the invention can be practiced by administering a BTK antisense oligonucleotide. Said antisense oligonucleotide may comprise at least 15, 25, 30, 35, 40 or 50 consecutive nucleotides of the human btk nucleotide sequence accessible in genebank under the numbers $NM_{13}000061$ (GI 4557376) (SEQ ID NO: 2) or complementary sequences thereof.

In a preferred embodiment, such antisense molecule can target the start codon region, the coding region, or the 3'-untranslated region of the BTK mRNA, and is able to specifically hybridize with one of said regions and inhibits the expression of BTK. In a particular embodiment, the antisense target the ATG region between nucleotide $C_{149}$ to $T_{180}$ of the NM_000061 sequence (SEQ ID NO: 2). More preferably, said antisense display the following sequence:

```
                                            (SEQ ID NO: 1)
   5' AGAATCACTGCGGCCATAGCTTCTTCTTTCTG 3'.
```

The antisense oligonucleotide may comprise at least one modified internucleoside linkage, for example a phosphorothioate linkage. It can also comprise at least one modified sugar moiety. Any chemical modification from the natural structure of oligonucleotide conferring an increased resistance to nucleases is encompassed.

The normal backbone of RNA and DNA is a 3' to 5' phosphodiester linkage but is susceptible to be degraded by exo or endonucleases when injected. Modified backbones elude this problem and include phosphorothioates, phosphorothioates, phosphorodithioates, phosphotriesters and alkyl phosphonates. Other modified backbones include chain alkyl or cycloalkyl internucleoside linkages, and chain heteroatomic or heterocyclic internucleoside linkages, such as morpholino linkages, siloxane backbones, sulfite based backbones, sulfonate or sulfonamide backbones and amide backbones. Antisense oligonucleotides according to the invention may also have inverted polarity such as a 3' to 3' linkage at the 3'-end. The man skilled in the art is able to obtain such chemically modified oligonucleotides following the teachings contained in U.S. Pat. Nos. 5,278,302, 5,286,717, 5,399,676, 5,466,677, 5,536,821, 5,672,697, 5,034,506, 5,235,033, 5,470,967, 5,596,086, 5,608,046 and U.S. Pat. No. 5,677,439. In the antisense according to the invention, it is also possible to incorporate Locked Nucleic Acids (LNAs) in which the 2'-hydroxyl group is linked to the 3' or 4' carbon atom of the sugar ring, see WO 99/14226. The antisense may also comprise modified nucleic acids such as 5-methylcytosine, 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thio substituted uracil, thymine and cytosine, as well as 5-substituted uracils and cytosines, see U.S. Pat. Nos. 3,687,808, 5,830,653, 5,763,588, and U.S. Pat. No. 6,005,096.

The antisense according to the invention can also be conjugated with at least one group enhancing to the bioavalability of the molecule including for example cholesterols, lipids, and phospholipids.

In this regard, the invention embraces an antisense oligonucleotide as depicted above. It concerns an antisense targeting the start codon region, the coding region, or the 3'-untranslated region of the BTK mRNA, and capable of specifically hybridizing with one of said regions and inhibiting the expression of BTK. Preferably, the antisense oligonucleotide comprises at least 15, 20, 25, preferably at least 30, or 50 consecutive nucleotides of the human btk nucleotide sequence accessible in genebank under the numbers $NM_{13}$ 000061 (GI 4557376) (SEQ ID NO: 2) or complementary sequences thereof.

In a preferred embodiment, the invention is aimed at such antisense molecule which target the ATG region between nucleotide $C_{149}$ to $T_{180}$ of the $NM_{13}$ 000061 sequence (SEQ ID NO: 2). More preferably, said antisense display the following sequence:

```
                                        (SEQ ID NO: 1)
5' AGAATCACTGCGGCCATAGCTTCTTCTTTCTG 3'.
```

It may comprise at least one chemical modification selected from modified internucleoside linkage, inverted polarity and nucleotide analogs as depicted above. It can also be conjugated with at least one group enhancing to the bioavalability of the molecule, such as cholesterols, lipids, and phospholipids.

The invention also relates to a vector for gene therapy expressing the above described antisense oligonucleotide.

Therefore, the invention is aimed at the method mentioned above comprising administering either a BTK inhibitor, a BTK antisense oligonucleotide or a vector expressing said antisense for the treating proliferative mastocytosis in mammalian, especially in human and in dogs. Category II, III and IV mastocytosis in human is especially contemplated. More particularly, the. method according to the invention is useful for treating solitary mastocytoma in human as well as dog mastocytoma and some rare subtypes like bullous, erythrodermic and teleangiectatic mastocytosis, mastocytosis with an associated hematological disorder, such as a myeloproliferative or myelodysplastic syndrome, or acute leukemia, myeloproliferative disorder associated with mastocytosis, and mast cell leukemia.

The invention embraces the use of the compounds, the antisense oligonucleotide or a vector as depicted above to manufacture a medicament for treating proliferative mastocytosis in mammalian, especially in human and in dogs. Category II, III and IV mastocytosis in human is especially contemplated as well as dog mastocytoma. More particularly, the method according to the invention is useful for treating solitary mastocytoma in human as well as dog mastocytoma and some rare subtypes like bullous, erythrodermic and teleangiectatic mastocytosis, mastocytosis with an associated hematological disorder, such as a myeloproliferative or myelodysplastic syndrome, or acute leukemia, myeloproliferative disorder associated with mastocytosis, and mast cell leukemia.

In a preferred embodiment, the method is applicable to the treatment of dog mastocyoma. Spontaneous mast cell tumors (MCT) are the most common malignant neoplasm in the dog, representing between 7% and 21% of all canine tumors, an incidence much higher than that found in humans. These tumors often behave in an aggressive manner, metastasizing to local lymph nodes, liver, spleen, and bone marrow.

In another preferred embodiment, the method is applicable to the treatment of mast cell leukemia in human.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

For treating category II, DI and IV mastocytosis, oral, intravenous and intramuscular route of administration are preferred.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

The pharmaceutical composition may be provided as a salt and can be formed with many acids, including but not limited to, hydrochloric, sulfuric, acetic, lactic, tartaric, malic, and succine, acids, etc. Salts tend to be more soluble in aqueous or other protonic solvents than are the corresponding free base forms. In other cases, the preferred preparation may be a lyophilized powder which may contain any or all of the following: 1-50 mM histidine, 0.1%-2% sucrose, and 2-7% mannitol, at a pH range of 4.5 to 5.5, that is combined with buffer prior to use.

Pharmaceutical compositions suitable for use in the invention include compositions wherein BTK inhibitors are contained in an effective amount to achieve the intended purpose. The determination of an effective dose is well within the capability of those skilled in the art. A therapeutically effective dose refers to that amount of active ingredient, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio of toxic to therpeutic effects is the therapeutic index, and it can be expressed as the ratio, LD50/ED50. Pharmaceutical compositions which exhibit large therapeutic indices are preferred.

In a still further embodiment, the invention is directed to a composition comprising a BTK inhibitor for topical application. Such composition is adapted for treating skin disorders such as solitary mastocytoma and bullous, erythrodermic and teleangiectatic mastocytosis.

The compositions according to the invention may be presented in all forms normally used for topical application, in particular in the form of a gel, paste, ointment, cream, lotion, liquid suspension aqueous, aqueous-alcoholic or, oily solutions, or dispersions of the lotion or serum type; or anhydrous or lipophilic gels, or emulsions of liquid or semi-solid consistency of the milk type, obtained by dispersing a fatty phase in an aqueous phase or vice versa, or of suspensions or emulsions of soft, semi-solid consistency of the cream or gel type, or alternatively of microemulsions, of microcapsules, of microparticles or of vesicular dispersions to the ionic and/or nonionic type. These compositions are prepared according to standard methods.

The composition according to the invention comprises any ingredient commonly used in dermatology and cosmetic. It may comprise at least one ingredient selected from hydrophilic or lipophilic gelling agents, hydrophilic or lipophilic active agents, preservatives, emollients, viscosity enhancing polymers, humectants, surfactants, preservatives, antioxidants, solvents, and fillers, antioxidants, solvents, perfumes, fillers, screening agents, bactericides, odor absorbers and coloring matter.

As oils which can be used in the invention, mineral oils (liquid paraffin), vegetable oils (liquid fraction of shea butter, sunflower oil), animal oils, synthetic oils, silicone oils (cyclomethicone) and fluorinated oils may be mentioned. Fatty alcohols, fatty acids (stearic acid) and waxes (paraffin, carnauba, beeswax) may also be used as fatty substances.

As emulsifiers which can be used in the invention, glycerol stearate, polysorbate 60 and the PEG-6/PEG-32/glycol stearate mixture are contemplated. As hydrophilic gelling agents, carboxyvinyl polymers (carbomer), acrylic copolymers such as acrylate/alkylacrylate copolymers, polyacrylamides, polysaccharides such as hydroxypropylcellulose, clays and natural gums may be mentioned, and as lipophilic is gelling agents, modified clays such as bentones, metal salts of fatty acids such as aluminum stearates and hydrophobic silica, or alternatively ethylcellulose and polyethylene may be mentioned.

As hydrophilic active agents, proteins or protein hydrolysates, amino acids, polyols, urea, allantoin, sugars and sugar derivatives, vitamins, starch and plant extracts, in particular those of Aloe vera may be used.

As lipophilic active, agents, retinol (vitamin A) and its derivatives, tocopherol (vitamin E) and its derivatives, essential fatty acids, ceramides and essential oils may be used. These agents add extra moisturizing or skin softening features when utilized.

In addition, a surfactant can be included in the composition so as to provide deeper penetration of the ingredients of the BTK inhibitor.

Among the contemplated ingredients, the invention embraces penetration enhancing agents selected for example from the group consisting of mineral oil, water, ethanol, triacetin, glycerin and propylene glycol; cohesion agents selected for example from the group consisting of polyisobutylene, polyvinyl acetate and polyvinyl alcohol, and thickening agents.

Chemical methods of enhancing topical absorption of drugs are well known in the art. For example, compounds with penetration enhancing properties include sodium lauryl sulfate (Dugard, P. H. and Sheuplein, R. J., "Effects of Ionic Surfactants on the Permeability of Human Epidermis: An Electrometric Study," J. Ivest. Dermatol., V.60, pp. 263-69, 1973), lauryl amine oxide (Johnson et. al., U.S. Pat. No. 4,411,893), azone (Rajadhyaksha, U.S. Pat. Nos. 4,405,616 and 3,989,816) and decylmethyl sulfoxide (Sekura, D. L. and Scala, J., "The Percutaneous Absorption of Alkylmethyl Sulfides," Pharmacology of the Skin, Advances In Biolocy of Skin, (Appleton-Century Craft) V. 12, pp. 257-69, 1972). It has been observed that increasing the polarity of the head group in amphoteric molecules increases their penetration-enhancing properties but at the expense of . increasing their skin irritating properties (Cooper, E. R. and Berner, B., "Interaction of Surfactants with Epidermal Tissues: Physiochemical Aspects," Surfactant Science Series, V. 16, Reiger, M. M. ed. (Marcel Dekker, Inc.) pp. 195-210, 1987).

A second class of chemical enhancers are generally referred to as co-solvents. These materials are absorbed topically relatively easily, and, by a variety of mechanisms, achieve permeation enhancement for some drugs. Ethanol (Gale et. al., U.S. Pat. No. 4,615,699 and Campbell et. al., U.S. Pat. Nos. 4,460,372 and 4,379,454), dimethyl sulfoxide (U.S. Pat. Nos. 3,740,420 and 3,743,727, and 4,575,515), and glycerine derivatives (U.S. Pat. No. 4,322,433) are a few examples of compounds which have shown an ability to enhance the absorption of various compounds.

The invention is also directed to a method for treating category IV mastocytosis including mast cell leukemia, comprising administering a BTK inhibitor as defined above or a BTK antisense or a vector expressing said antisense and a compound selected from 2-Chloro-2'-desoxyadenosine and analogs thereof to a mammalian in need of such treatment. In this regard, the invention also contemplates a product comprising a BTK inhibitor, a BTK antisense or a vector expressing said antisense and at least one compound selected from 2-Chloro-2'-desoxyadenosine and analogs thereof for a separate, sequential or simultaneous use for treating category IV mastocytosis including mast cell leukemia as well as dog mastocytoma.

2-Chloro-2'-desoxyadenosine (2-CDA), Cladribine, Merck Index (12th ed.) #2397 has the following formula:

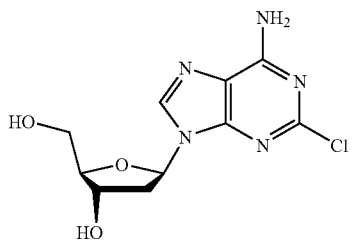

Regarding systemic forms of mastocytosis, especially category III mastocytosis, the invention also relates to a method as mentioned above, comprising administering a BTK inhibitor, a BTK antisense or a vector expressing said antisense and IFNα to a human in need of such treatment.

In this regard, the invention also contemplates a product comprising a BTK inhibitor, a BTK antisense or a vector expressing said antisense and IFNα for a separate, sequential or simultaneous use for treating systemic forms of mastocytosis, especially category III mastocytosis.

Utility of the invention will further ensue from the detailed description below.

EXAMPLE 1 cDNA Expression Arrays of Normal Mast Cells Versus Proliferating Mast Cells

The purpose of the research conducted in frame with the present invention was to identify genes that are over-expressed in mast cell lines displaying mutations on the c-kit receptor. Indeed, mutation in the c-kit receptor is responsible for abnormal proliferation of mast cells, ultimately leading to mastocytosis for which the Applicant filed U.S. 60/301,406. The idea underlying the invention is to find other targets for depleting proliferative mast cells. In case where a given over-expressed gene is shown to be involved in the regulation or the proliferation of mast cells, it becomes a good candidate as pharmacological target.

Transcriptomes of CD34+ cells, immature hematopoietic cells that are differentiating, normal mature mast cells and mast cells bearing mutations on the c-kit receptors were performed in this regard.

1.1 cDNA Expression Arrays

First, we have characterized the expression profile of the HMC-1 cell lines expressing mutated c-kit on the 560 and 816 positions. We also performed expression profiles on KG1a cells, which are the closest cells from primary CD34+ cells.

We used membranes from CLONETECH in which 588 pre-selected genes were spotted.

Results of these experiments are depicted in FIG. 1.

We did similar analysis with CD34+ cells extracted from human bone marrow, mature mast cells derived thereof, as well as another HMC-1 cell line displaying a differentiation state above the cell line used initially.

The results are displayed in Table 1 below showing the differential expression of genes of mature mast cells compared to CD4+ cells.

TABLE 1 mast cells genomics

| code | Ratio | Diff | Comparison between mast cells and CD34+ cells |
|---|---|---|---|
| | | | Genes under-expressed in mast cells versus CD34+ Protein/gene |
| A2j | 0.031288 | −39630 | cyclin B1 |
| A5e | 0.040922 | −33257 | PCNA; cyclin |
| A2i | 0.050378 | −22356 | cyclin A |
| D2j | 0.155342 | −17552 | laminin 3-kDa RECEPTOR |
| E3f | 0.249099 | −25430 | c-myc transcription factor (puf); nucleoside diphosphate kinase B (EC 2.7.4.6) (NDK B) (NDP kinase B; NM23-H2 |
| G13 | 0.425034 | −15186 | tubulin alpha |
| G12 | 0.464288 | −32777 | liver glyceraldehyde 3-phosphate dehydrogenase |
| | | | Genes sur exprimés dans mastocyte/CD34+ Protein/gene |
| E2b | 2.775687 | 14344 | TIMP-1; erythroid potentiating activity (EPA) |
| C6c | 2.799637 | 20847 | insulin-like growth factor binding protein 2 |
| F2g | 2.816442 | 22691 | endothelin ET2 |
| F3j | 4.008417 | 26450 | transcription factor ETR103; early growth response protein 1 (EGR-1) (KROX24); zinc finger protein 225 (AT225) |
| C3i | 4.694429 | 27590 | Notch4 |
| E2d | 5.850825 | 16454 | TIMP-3; mitogen-inducible gene 5 (mig-5) |
| C3j | 6.289161 | 16005 | Jagged 1 |
| F6e | 6.525074 | 14984 | platelet-derived growth factor A chain (PDGF-A) |
| B6b | 7.194957 | 30219 | C-kit |
| B6c | 7.476532 | 26217 | proto-oncogene c-src1 tyrosine kinase domain |
| E1f | 9.513902 | 18986 | MMP-9; gelatinase B |
| D6h | 10.915376 | 16638 | LAR |
| B6a | 11.612540 | 13202 | C-fos |
| E1n | 23.914141 | 13611 | MMP-17 (MT4-MMP) |

We show a strong over-expression of the c-kit receptor but also an over-expression of metalloproteases such as MMP-9 and MMP-17.

Transcriptomes performed using the same experimental procedures and the HMC-1 cell line result in the following observations :

a strong over-expression of genes linked to cellular proliferation (PCNA, Grb2, NDP kinase B). It is worth noting that Grb2 is involved in the activation of the Ras-MAP kinases pathway mainly acting as an effector protein on Sos, which in turn activates Ras. NDP kinase B acts as a transcriptional factor of the c-myc oncogene.

Grb2-Sos→Ras→Raf→MAPKK→MAPK→JUN→transcription

A strong over-expression of genes involved in the dynamic of the cytoskeleton (Rho A, Rho C, Rho GDI).

Figure 2:
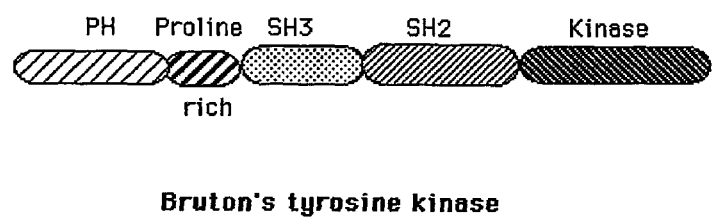

A strong over-expression of the Bruton Tyrosine Kinase (BTK). BTK is a cytoplasmic tyrosine kinase displaying three domains (SH2-SH3, PH, see FIG. 2), which is involved in the activation and the differentiation of B lymphocytes. BTK is activated by the autophosphorylation induced by the SRC kinases. BTK also has an inhibition activity of the Fas-dependent apoptotic pathway. Furthermore, mutations in BTK have been shown to lead to the agammaglobulinemia X syndrome.

1.2 In addition, we performed differential expression arrays comparing the level of expression of genes in the HMC-1 cell line in regards to the level of expression of genes in normal mature mast cells.

In this case, the observed differences were mainly linked to the activation of the c-kit receptor bearing the double mutation. Results are displayed in Table 2 below.

We show a strong under-expression of genes characterizing mature mast cells and a strong over-expression of genes involved in cellular proliferation such as the cyclines, the weel kinase, as well as PCNA, Grb2, etc . . . , as mentioned above.

We also observed a very strong over-expression of the VEGF (FLT-1) receptor.

The most striking result of the above differential transcriptome is the observation of a strong specific over-expression of the Bruton's Tyrosine Kinase (BTK) in the HMC-1 cell line.

Indeed, if we normalize the level of expression of this protein, we obtain the following results:

| Cells | BTK expression level |
|---|---|
| CD34+ | 0 |
| KG1 | 0 |
| Mastocyte | 1 |
| HMC-1 (ND) | 6 |
| HMC-1(D) | 12 |

TABLE 2

| Code | Ratio | Diff | Comparison between HMC-1 and mature mast cells |
|---|---|---|---|
| | | | Genes under-expressed in HMC-1 versus mature mast cells Protein/gene |
| E1f | 0.038560 | −33635 | MMP-9; gelatinase B |
| D4d | 0.038976 | −19824 | integrin alphaE |
| B6c | 0.057729 | −47025 | proto-oncogene c-src1 tyrosine kinase domain |
| A7l | 0.057749 | −17752 | type II cytoskeletal 8 keratin; cytokeratin 8 (K8; CK 8) |
| C3i | 0.065525 | −54022 | Notch4 |
| C3j | 0.080110 | −28868 | Jagged 1 |
| F6c | 0.091018 | −14411 | NT-4 (NT-5) + NT-6 |
| B6a | 0.104315 | −21337 | C-fos |
| D6h | 0.112012 | −26819 | LAR |
| A7m | 0.121580 | −50987 | vimentin |
| A4m | 0.153099 | −18310 | stress-activated protein kinase JNK2 (EC 2.7.1.-); C-JUN N-terminal kinase (JNK-55) |
| E1m | 0.161202 | −19648 | MMP-17(MT4-MMP) |
| C7c | 0.170346 | −20295 | high affinity nerve growth factor receptor precursor (EC 2.7.1.112); TRK1 transforming tyrosine kinase protein (P140-TRKA) + trk-T3 (P68 trk-T3 oncoprotein) |
| B6b | 0.292221 | −40962 | C-kit |
| E2d | 0.312657 | −22494 | TIMP-3; mitogen-inducible gene 5 (mig-5) |
| F6e | 0.316690 | −19939 | platelet-derived growth factor A chain (PDGF-A) |
| E2b | 0.334208 | −24617 | TIMP-1; erythroid potentiating activity (EPA) |
| F3j | 0.475943 | −30454 | transcription factor ETR103; early growth response protein 1 (EGR-1). (KROX24); zinc finger protein 225 (AT225) |
| D5f | 2.065336 | 22681 | CD9 |
| B5b | 3.017291 | 18317 | glutathione-S-transferase homolog |
| A3n | 3.120643 | 15820 | CDC10 protein homolog |
| B5l | 3.135585 | 42370 | proto-oncogene rhoA multidrug resistance protein; GTP-binding protein (rhi |
| E3f | 3.510638 | 34928 | c-myc transcription factor (puf); nucleoside diphosphate kinase B (EC 2.7.4. (NDK B) (NDP kinase B; NM23-H2 |
| A6c | 3.600842 | 31491 | GRB2 isoform (growth factor receptor-bound protein 2); ASH protein |
| B7b | 3.737622 | 22339 | RBA/p48 |
| B7i | 4.130294 | 31929 | tyrosine-protein kinase BTK (EC 2.7.1.112); bruton's tyrosine kinase; agammaglobulinaemia tyrosine kinase (ATK); B cell progenitor kinase (BPK) (BTK) (AGMX1) |
| C3d | 4.325706 | 21657 | HHR6A (yeast RAD 6 homolog) |
| F6d | 4.463241 | 17053 | PDGF associated protein |
| A4a | 4.520753 | 14590 | CDC27HS Protein |
| B3n | 5.035878 | 14061 | PDCD2 |
| F4b | 5.767336 | 15675 | IFN-gamma antagonist cytokine |
| E3m | 8.291140 | 13824 | rhoC (H9); small GTPase (rhoC) |
| A3j | 8.622708 | 14971 | CDK tyrosine 15-kinase WEE1HU (WEE1HU) |
| A2i | 13.215747 | 23894 | cyclin A |
| A2j | 14.293561 | 28076 | cyclin B1 |
| A5e | 17.381624 | 38333 | PCNA; cyclin |
| D7m | 20.767223 | 37874 | VEGF receptor 1 precursor, EC 2.7.1.112; tyrosine-protein kinase receptor FLT (FLT-1) (SFLT) |

This strong over-expression of BTK has been also confirmed by Northern and Western blots.

EXAMPLE 2

BTK as a Pharmacological Target 2.1 We used antisense RNA to inhibit the expression of BTK in HMC-1, which is resistant to apoptosis. In this regard, we have constructed a retrovirus vector coding for an antisense RNA containing 32 nucleotides directed to the sequence comprised in the AUG region of the BTK gene (SEQ ID No 1).

Figure 3:
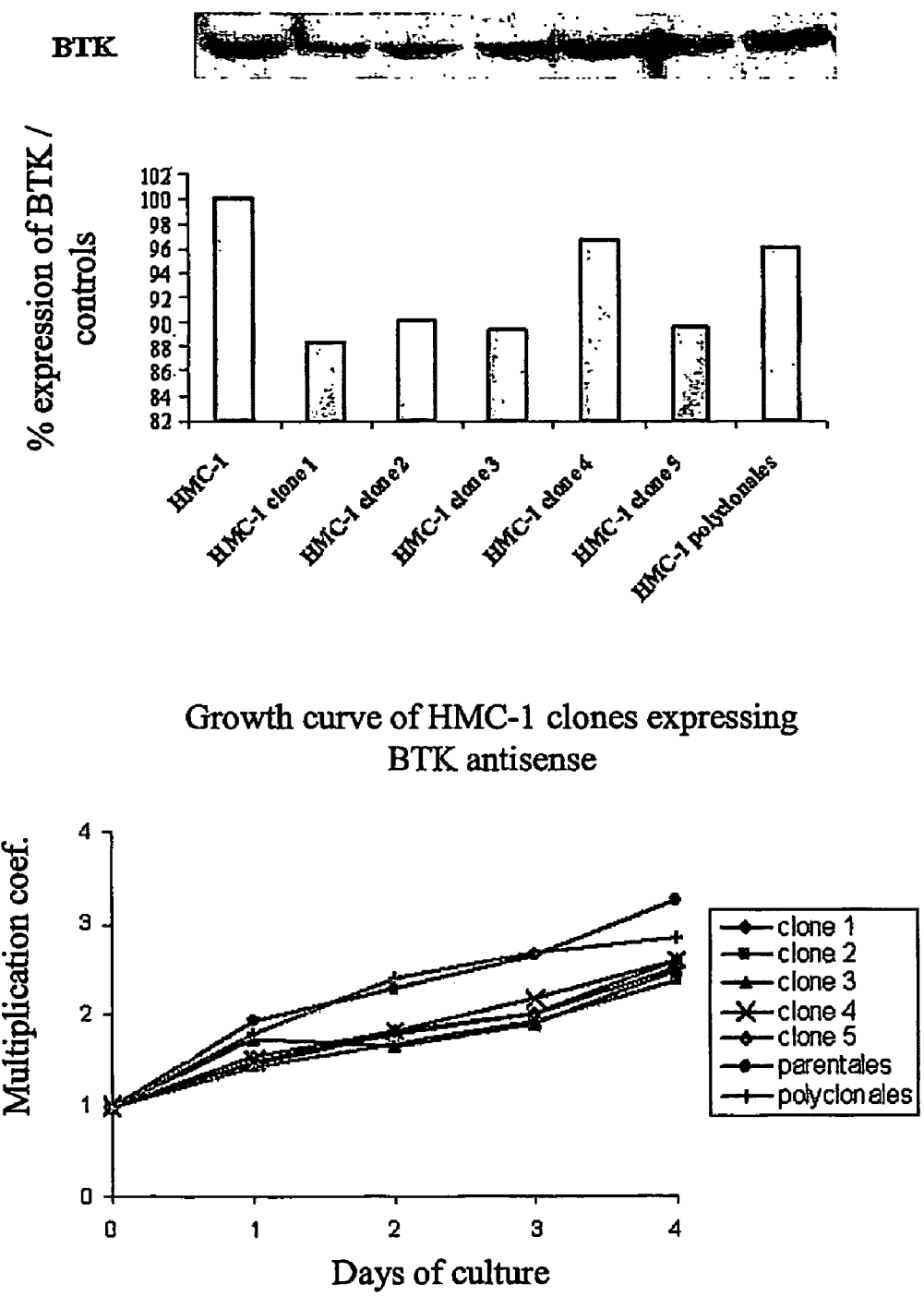

Target cells, which integrated this vector, show a significant decrease in the expression of BTK. Regarding 4 clones, we have noted a decrease of about 50% of the expression of the BTK (see FIG. 3).

Figure 4:
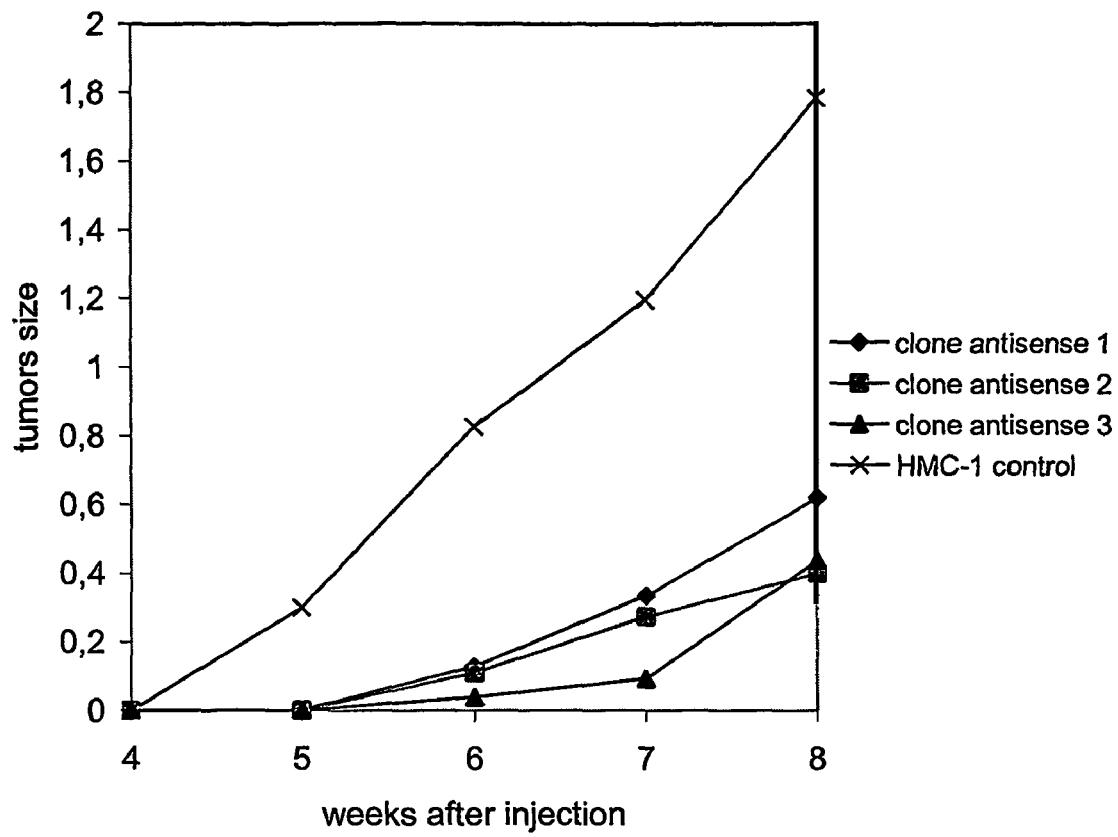

2.2 We also did experiments showing that the expression of the BTK antisense has significant anti-tumoral effects. We used nude mice, which have been injected with 2 millions HMC-1 cells. The size of the tumors has been assessed few weeks after injection, as shown in FIG. 4.

EXAMPLE 3

BTK Antisense RNA Abrogates BTK Mediated Apoptosis Protection 3.1 Preparation of Vectors Allowing the Expression of the BTK Antisense RNA We used 3 different plasmids:
The pLNCX retroviral vector has integrated the sequence coding for the BTK antisense RNA which targets the AUG region of the BTK gene. This vector also contains transposon 5 which confers resistance to geneticine and a Psi sequence allowing the encapsulation of the DNA in viral particles.
The pN8-epsilon vector containing the Gag-Pol sequence of Mo-MuLV coding for viral particles (available from Invitrogene).
The pN8-epsilon vector containing the Env-VSVG sequence coding for viral envelope (Available from Invitrogene).

Transfection of cells is realized using Exgen® (Euromedex, France) following the instructions of the manufacturer. Basically, 500000 293 EBNA cells are plated/wells the day before transfection in six wells plates. The next day, a mixture of 0.5 µg of each vector is added to the cells together with Exgen® (7.5 µl/wells). 24 hours after transfection, the mixture is washed out and the cells are washed in PBS and cultured in fresh media. Culture supernatants containing viral particles are collected at 48, 72 and 96 hours after transfection, and gathered, filtered at 0.45 µm, concentrated by ultracentrifugation and then kept in PBS-BSA 1% at −80° C. pour later processing.

3.2 Titration of Viral Supernatants.

Supernatants are titrated by infecting NIH-3T3 cells plated at 50,000 cells/wells in 6 wells plates. Infection of NIH-3T3 cells is performed in presence of 4 µg/ml polybrene (Sigma, France). 24 hours after infection, the cells are washed in PBS and cultured in media containing geneticine (0.8 mg/ml). The viral load is determined by the number of colonies resistant to G418 after 8 days of culture. Viral supernatants containing either the virus coding only for G418 resistance (LNCX) or virus coding for G418 resistance and the antisense directed against the BTK AUG (LNCX-ASBTK) both display a titer comprised between $5.10^8$ and $6.10^8$ viral particles on NIH-3T3 cells.

3.3 Obtention of Clones of HMC1 Cells Expressing the Antisense Directed Against the BTK AUG.

-Determination of HMC1 cells sensibility to G418.

To determine, the lethal geneticine dose for HMC1, cells were seeded in 6 wells plate (105 cells/wells) in presence of increasing concentration of geneticine (0; 0.6; 0.8; 1; 1.2; 1.4 mg/ml). One week after seeding, colonies are visualized by crystal purple coloration. It appears that the effective dose was 1.2 mg/ml geneticine in the culture Media. Indeed, at lower doses, we observed development of HMC1 colonies.

-Infection of HMC1 Cells

HMC1 cells seeded the day before in 6 wells plates ($10^5$ cells/ well) are infected with increasing doses of LNCX or LNCX-AS BTK virus. 24 hours after infection, cells are washed in PBS and cultured in medium containing geneticine (1.2 mg/ml). After one week, we observed the formation of colonies resistant to geneticine and whose number depends on the quantity of virus used for infection. When comparing the number of colonies of HMC1 resisting to G418 obtained from cells infected with the LNCX or LNCX-AS BTK virus, we observed independently of the virus concentration used, a lower number of colonies of cells infected with LNCX-AS BTK relative to the number of colonies of cells infected with LNCX. For equivalent quantity of virus, we obtained between 5 to 10 fold less colonies of HMC resisting to G418 by infecting with the LNCX-AS BTK virus compared to the infection with the LNCX "empty".

In conclusion, a decrease of BTK expression by the specific antisense RNA leads to a strong cellular mortality (80 to 90% mortality). This result confirms the hypothesis according to which BTK protects HMC1 cells from apoptosis.

The 10 to 20% surviving clones are those for which the antisense expression level is weak thereby maintaining a BTK expression level compatible with cellular survival.

The invention claimed is:

1. A method for treating proliferative mastocytosis comprising administering a therapeutically effective amount of a Bruton tyrosine kinase (BTK) antisense oligonucleotide or a vector for expressing a BTK antisense oligonucleotide to a mammal having proliferative mastocytosis in need of such treatment, wherein the BTK antisense oligonucleotide is complementary to at least 25 consecutive nucleotides of SEQ ID NO: 2 and wherein the BTK antisense oligonucleotide inhibits expression of BTK in proliferative mast cells and depletes proliferative mast cells.

2. The method according to claim 1, wherein said antisense oligonucleotide is complementary to at least 30 consecutive nucleotides of SEQ ID NO: 2.

3. The method according to claim 2, wherein said antisense oligonucleotide targets a start codon region, a coding region, or a 3'-untranslated region of a BTK mRNA, and is able to specifically hybridize with one of said regions and inhibits the expression of BTK.

4. The method according to claim 3, wherein said antisense oligonucleotide comprises at least one chemical modification selected from modified internucleoside linkage, inverted polarity and nucleotide analogs.

5. The method according to claim 3, wherein said antisense oligonucleotide is conjugated with at least one group enhancing the bioavailability of the antisense oligonucleotide.

6. The method according to claim 1, wherein the mammal is a human or a dog.

7. The method according to claim 6, wherein the proliferative mastocytosis is a category II, III or IV mastocytosis and the mammal is a human.

8. The method according to claim 6, wherein the proliferative mastocytosis is a mastocytoma and the mammal is a dog.

9. The method according to claim 6, wherein the proliferative mastocytosis is a solitary mastocytoma and the mammal is a human.

10. The method according to claim 6, wherein the proliferative mastocytosis is a bullous, erythrodermic or teleangiectatic mastocytosis, mastocytosis with an associated hematological disorder or a myeloproliferative disorder associated with mastocytosis.

11. The method according to claim 6, wherein the proliferative mastocytosis is a mast cell leukemia.

12. A method for treating a category IV mastocytosis comprising administering to a mammal a therapeutically effective amount of (a) a compound selected from 2-Chloro-T-desoxyadenosine and analogs thereof and (b) a Bruton tyrosine kinase (BTK) inhibitor or a BTK antisense oligonucleotide or a vector for expressing a BTK antisense oligonucleotide to a mammal in need of such treatment, wherein the BTK antisense oligonucleotide is complementary to at least 25 consecutive nucleotides of SEQ ID NO: 2.

13. A method for treating a category III mastocytosis comprising administering to a human a therapeutically effective amount of (a) interferon alpha (IFNα) and (b) a Bruton tyrosine kinase (BTK) inhibitor or a BTK antisense oligonucleotide or a vector for expressing a BTK antisense oligonucleotide to a mammal in need of such treatment, wherein the BTK antisense oligonucleotide is complementary to at least 25 consecutive nucleotides of SEQ ID NO: 2.

14. The method according to claim 1, comprising administering both a BTK inhibitor and the BTK antisense oligonucleotide.

15. The method according to claim 14, wherein the BTK inhibitor is selected from malononitrilamides.

16. The method according to claim 15, wherein the BTK inhibitor is selected from leflunomide analogs.

17. The method according to claim 15, wherein the BTK inhibitor is selected from:
1-cyano-2-hydroxy-N[4-(methylsulfonyl)phenyl]but-2-enamide, 1-cyano-2-hydroxy-N[3-(methylsulfonyl)phenyl]but-2-enamide, and N[3-bromo-4-(trifluoromethoxy)phenyl]-1-cyano-2-hydroxybut-2-enamide.

* * * * *